United States Patent

Fukada et al.

[11] Patent Number: 6,083,873
[45] Date of Patent: Jul. 4, 2000

[54] HERBICIDAL COMPOSITION

[75] Inventors: Noriyuki Fukada; Toshio Kitajima; Shinichiro Koyanagi, all of Tokuyama, Japan

[73] Assignee: Tokuyama Corporation, Yamaguchi-ken, Japan

[21] Appl. No.: 09/145,028

[22] Filed: Sep. 1, 1998

[30] Foreign Application Priority Data

Sep. 3, 1997 [JP] Japan .................................. 9-238710

[51] Int. Cl.$^7$ .................................................. A01N 25/32
[52] U.S. Cl. ............................................ 504/105; 504/107
[58] Field of Search ...................................... 504/105, 107

[56] References Cited

U.S. PATENT DOCUMENTS

| | | | |
|---|---|---|---|
| 4,124,372 | 11/1978 | Pallos et al. | 71/88 |
| 4,256,481 | 3/1981 | Gardi et al. | 71/88 |
| 4,448,960 | 5/1984 | Rohr et al. | 544/282 |
| 4,565,565 | 1/1986 | Rohr et al. | 71/92 |
| 4,600,433 | 7/1986 | Alt | 71/118 |
| 4,622,061 | 11/1986 | Alt | 71/88 |
| 4,895,587 | 1/1990 | Kato et al. | 71/90 |
| 4,995,899 | 2/1991 | Scholz et al. | 71/92 |
| 5,201,933 | 4/1993 | Miller et al. | 504/104 |
| 5,484,760 | 1/1996 | Bussler et al. | 504/103 |

FOREIGN PATENT DOCUMENTS

| | | |
|---|---|---|
| 0009091 | 4/1980 | European Pat. Off. . |
| 0031042 | 7/1981 | European Pat. Off. . |
| 0065724 | 12/1982 | European Pat. Off. . |
| 0206251 | 12/1986 | European Pat. Off. . |
| 0229649 | 7/1987 | European Pat. Off. . |
| 2448857 | 9/1980 | France . |
| 55-94303 | 7/1980 | Japan . |
| 56-99481 | 8/1981 | Japan . |
| 515699 | 3/1993 | Japan . |

*Primary Examiner*—S. Mark Clardy

[57] ABSTRACT

A herbicidal composition containing an ethenylamide compound as a herbicidally effective component and a dichloroacetamide compound as a safener.

7 Claims, No Drawings

HERBICIDAL COMPOSITION

The present invention relates to a herbicidal composition comprising an ethenylamide compound and a dichloroacetamide compound.

It is known that ethenylamide compounds have excellent herbicidal activity against the weeds of the grass family (JP-B 5-15699) (the term "JP-B" as used herein means an "examined Japanese patent publication"). Out of the ethenylamide compounds, an ethenylamide compound having an aryl group or heteroaryl group at the 1-position of an ethenyl group can be used as a herbicide for broad-leaved crops such as soybeans, cotton and beet, and the crops of the grass family such as wheat, barley, corn and upland rice. However, when an ethenylamide compound is used as a herbicide, the crops may be damaged by the herbicide, for example, the leaves of cultivated crops may die or yellow, the growth of the crops may be suppressed, or the yield may drop according to the type, the amount of water, temperature and the like of the soil of the crop cultivating land.

Generally speaking, as one of the means of reducing phytotoxicity of herbicides is use of a safener. For example, U.S. Pat. No. 5,484,760 teaches that dichloroacetamide, alkoxyiminobenzene acetonitrile, thiazole carboxylate and naphthalene compounds having a safener function are effective for thiourea, imidazole, haloacetamide and thiocarbamate herbicides.

JP-A 55-94303 and JP-A 56-99481 (the term "JP-A" as used herein means an "unexamined published Japanese patent application") disclose that a dichloroacetamide compound has a function to reduce phytotoxicity of acetoanilide and thiol carbamate herbicides.

However, the mechanism of phytotoxic action of a herbicide and the mechanism of the suppression of phytotoxicity by a safener are unknown at the present. The present situation is that what phytotoxicity occurs and which safener is effective for suppressing the phytotoxicity must be investigated based on the rule of trial and error for each type of herbicide used.

As the background of the present invention, the inventors of the present invention have discovered that a specific ethenylamide compound causes phytotoxic action to crops. As a matter of course, any compound having a function to reduce phytotoxicity of the specific ethenylamide compound herbicide has been unknown up till now.

It is therefore an object of the present invention to provide a safener which makes it possible to use a specific ethenylamide compound which causes phytotoxic action to crops, as a herbicide advantageously by reducing phytotoxicity while maintaining its herbicidal effect.

It is another object of the present invention to provide a herbicidal composition which comprises an ethenylamide compound and the above safener, and exhibits a marked effect on many kinds of weeds without doing any phytotoxic action to cultivated crops.

Other objects and advantages of the present invention will become apparent from the following description.

According to the present invention, the above objects and advantages of the present invention can be attained by a herbicidal composition which comprises:

an ethenylamide compound represented by the following formula (1) as a herbicidally effective component:

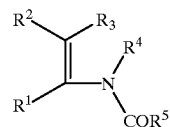

(1)

wherein $R^1$ is a heteroaryl group having 3 to 8 ring member carbon atoms and 1 to 2 hetero atoms selected from the group consisting of oxygen atom, sulfur atom and nitrogen atom, or aryl group having 6 to 14 carbon atoms, the heteroaryl group and the aryl group may be substituted by at least one substituent selected from the group consisting of an alkyl group having 1 to 3 carbon atoms, a halogen atom, an alkoxyl group having 1 to 3 carbon atoms, an alkylthio group having 1 to 3 carbon atoms, cyano group, nitro group and amino group; $R^2$ and $R^3$ are independently hydrogen atom or an alkyl group having 1 to 12 carbon atoms, or may be bonded together with the carbon atom, to which they are bonded, to form a ring having 5 to 6 ring member carbon atoms; $R^4$ is an alkyl group having 1 to 12 carbon atoms, an alkenyl group having 2 to 12 carbon atoms, an alkynyl group having 2 to 12 carbon atoms, an aryl group having 6 to 14 carbon atoms, a heteroaryl group having 3 to 8 carbon atoms, a cycloalkyl group having 3 to 6 carbon atoms, a cycloalkenyl group having 4 to 6 carbon atoms or a heterocycloalkyl group having 4 to 5 carbon atoms, all of these groups may be substituted by at least one substituent selected from the group consisting of an alkyl group having 1 to 3 carbon atoms, a halogen atom, an alkoxyl group having 1 to 3 carbon atoms, an alkylthio group having 1 to 3 carbon atoms, cyano group, nitro group and amino group (provided that when $R^4$ is an alkyl group having 1 to 12 carbon atoms or an alkenyl group having 2 to 12 carbon atoms, the substituent cannot be an alkyl group having 1 to 3 carbon atoms); and $R^5$ is a heteroaryl group having 3 to 8 ring member carbon atoms and 1 to 2 hetero atoms selected from the group consisting of oxygen atom, sulfur atom and nitrogen atom, an aryl group having 6 to 14 carbon atoms or an alkyl group having 1 to 12 carbon atoms, all of these groups may be substituted by at least one substituent selected from the group consisting of an alkyl group having 1 to 3 carbon atoms, a halogen atom, an alkoxyl group having 1 to 3 carbon atoms, an alkylthio group having 1 to 3 carbon atoms, cyano group, nitro group and amino group (provided that when $R^5$ is an alkyl group having 1 to 12 carbon atoms, the substituent cannot be an alkyl group having 1 to 3 carbon atoms); and a dichloroacetamide compound as a safener.

The herbicidal composition of the present invention comprises an ethenylamide compound represented by the above formula (1) (may be referred to as "ethenylamide compound of formula 1" hereinafter) as a herbicidally effective component. The herbicidally effective component refers to a component having herbicidal activity, and it is known that the ethenylamide compound of formula 1 has herbicidal activity (see JP-B 5-15699). A description is subsequently given of the ethenylamide compound of formula 1.

In the formula (1), $R^1$ is a heteroaryl group having 3 to 8 ring member carbon atoms and 1 to 2 hetero atoms selected from the group consisting of oxygen atom, sulfur atom and nitrogen atom, or an aryl group having 6 to 14 carbon atoms.

Illustrative examples of the heteroaryl group include furyl group, thienyl group, pyrrolyl group, pyridyl group, pyrimidinyl group, benzofuryl group, benzothienyl group, indolyl group, quinolyl group, thiazolyl group, pyrazolyl group, oxazolyl group, benzoxazolyl group and the like, and those of the aryl group include phenyl group, naphthyl group, anthranyl group, phenanthrenyl group and the like.

The heteroaryl group and the aryl group may be substituted by at least one substituent selected from the group consisting of an alkyl group having 1 to 3 carbon atoms, a halogen atom, an alkoxyl group having 1 to 3 carbon atoms, an alkylthio group having 1 to 3 carbon atoms, cyano group, nitro group and amino group. Illustrative examples of the substituent include alkyl groups such as methyl group, ethyl group and propyl group, halogen atoms such as chlorine atom, bromine atom, iodine atom and fluorine atom; alkoxyl groups such as methoxy group, ethoxy group and propoxy group; alkylthio groups such as methylthio group, ethylthio group and propylthio group, cyano group, nitro group and amino group.

Illustrative examples of the aryl group and heteroaryl group substituted by these substituents include methylphenyl group, ethylphenyl group, propylpheyl group, butylphenyl group, hexylphenyl group, dimethylphenyl group, methyl(ethyl)phenyl group, ethyl(propyl)phenyl group, chlorophenyl group, bromophenyl group, fluorophenyl group, dichlorophenyl group, methoxyphenyl group, ethoxyphenyl group, propoxyphenyl group, dimethoxyphenyl group, cyanophenyl group, nitrophenyl group, chloro(methyl)phenyl group, methoxy(methyl)phenyl group, methylthiophenyl group, (trifluoromethyl)phenyl group, (amino)di methylphenyl group, chloro(nitro)phenyl group, methylnaphthyl group, chloronaphthyl group, methoxynaphthyl group, dimethylnaphthyl group, methylfuryl group, methoxythienyl group, chlorothienyl group, methylthienyl group, methylpyrrolyl group, chloropyrrolyl group, methylpyridyl group, chloropyridyl group, dimethoxypyrimidinyl group, methylpyrimidinyl group, chloropyrimidinyl group, methylbenzofuryl group, methoxybenzofuryl group, chlorobenzofuryl group, methylbenzothienyl group, methylindolyl group, methylquinolyl group, methylthiazolyl group, methylpyrazolyl group, methyloxazolyl group, methylbenzoxazolyl group and the like.

In the formula (1), $R^2$ and $R^3$ are independently a hydrogen atom or alkyl group having 1 to 12 carbon atoms, or may be bonded together with the carbon atom, to which they are bonded, to form a ring having 5 to 6 carbon atoms.

Illustrative examples of the alkyl group include methyl group, ethyl group, propyl group, butyl group, pentyl group, hexyl group, heptyl group, octyl group, nonyl group, decyl group and the like. The ring formed by bonding $R^2$ and $R^3$ together is a cycloalkyl ring such as cyclopentyl or cyclohexyl.

In the formula (1), $R^4$ is an alkyl group having 1 to 12 carbon atoms, an alkenyl group having 2 to 12 carbon atoms, an alkynyl group having 2 to 12 carbon atoms, an aryl group having 6 to 14 carbon atoms, a heteroaryl group having 3 to 8 carbon atoms, a cycloalkyl group having 3 to 6 carbon atoms, a cycloalkenyl group having 4 to 6 carbon atoms or a heterocycloalkyl group having 4 to 5 carbon atoms.

Examples of the alkyl group include methyl group, ethyl group, propyl group, butyl group, pentyl group, hexyl group, heptyl group, octyl group, nonyl group, decyl group and the like. Examples of the alkenyl group include propenyl group, butenyl group, pentenyl group, hexenyl group, octenyl group and the like. Examples of the alkynyl group include propynyl group and butynyl group. Examples of the aryl group include phenyl group, naphthyl group, anthranyl group and phenanthrenyl group. Examples of the heteroaryl group include furyl group, thienyl group, pyrrolyl group, pyridyl group, pyrimidinyl group, benzofuryl group, benzothienyl group, indolyl group, quinolyl group, thiazolyl group, pyrazolyl group, oxazolyl group, benzoxazolyl group and the like. Examples of the cycloalkyl group include cyclopropyl group, cyclobutyl group, cyclopentyl group, cyclohexyl group, cycloheptyl group and the like. Examples of the cycloalkenyl group include cyclopentenyl group, cyclohexenyl group and the like. Examples of the heterocycloalkyl group include tetrahydrofuryl group, tetrahydrothienyl group, pyrrolidyl group and the like.

All of these groups represented by $R^4$ may be substituted by at least one substituent selected from the group consisting of an alkyl group having 1 to 3 carbon atoms, a halogen atom, an alkoxyl group having 1 to 3 carbon atoms, an alkylthio group having 1 to 3 carbon atoms, cyano group, nitro group and amino group, provided that when $R^4$ is an alkyl group having 1 to 12 carbon atoms or an alkenyl group having 2 to 12 carbon atoms, the substituent cannot be an alkyl group having 1 to 3 carbon atoms. Illustrative examples of these substituents are the same as those listed for $R^{1.}$ Illustrative examples of the substituted alkyl group substituted by the above substituents include fluoromethyl group, trifluoromethyl group, chloromethyl group, chloroethyl group, bromoethyl group, chloropropyl group, chlorohexyl group, methoxymethyl group, methoxyethyl group, methoxypropyl group, methoxybutyl group, ethoxymethyl group, ethoxyethyl group, ethoxypropyl group, butoxymethyl group, butoxyethyl group, phenoxymethyl group, phenoxyethyl group, cyanopropyl group, cyanobutyl group, nitroethyl group, nitropropyl group, ethylthiomethyl group, propiothiomethyl group, methylthioethyl group, ethylthioethyl group, N,N-diethylaminoethyl group, N,N-diethylaminopropyl group, phenylmethyl group, phenylethyl group, methoxythienylmethyl group, methoxycarbonylmethyl group, methoxycarbonylethyl group, ethoxycarbonylethyl group and the like. Illustrative examples of the substituted alkenyl group include chloropropenyl group, cyanobutenyl group, methoxypentenyl group and the like, and illustrative examples of the substituted alkynyl group include chloropentynyl group, ethoxybutynyl group, nitrohexynyl group and the like.

Illustrative examples of the substituted aryl group, substituted heteroaryl group, substituted cycloalkyl group, substituted cycloalkenyl group and substituted heterocycloalkyl group include methylphenyl group, ethylphenyl group, propylphenyl group, butylphenyl group, hexylphenyl group, dimethylphenyl group, ethyl(methyl)phenyl group, ethyl (propyl)phenyl group, chlorophenyl group, bromophenyl group, fluorophenyl group, dichlorophenyl group, methoxyphenyl group, ethoxyphenyl group, propoxyphenyl, dimethoxyphenyl group, cyanophenyl group, nitrophenyl group, chloro(methyl)phenyl group, methoxy(methyl) phenyl group, methylthiophenyl group, (trifluoromethyl) phenyl group, (dimethyl)aminophenyl group, chloro(nitro) phenyl group, methylnaphthyl group, chloronaphthyl group, methoxynaphthyl group, dimethylnaphthyl group, methylfuryl group, methoxythienyl group, chlorothienyl group, methylthienyl group, methylpyrrolyl group, chloropyrrolyl group, methylpyridyl group, chloropyridyl group, dimethoxypyrimidinyl group, methylpyrimidinyl group, chloropyrimidinyl group, methylbenzofuryl group, methoxybenzofuryl group, chlorobenzofuryl group, methylbenzothienyl group, methylindolyl group, methylquinolyl group, methylthiazolyl group, methylpyrazolyl group, methyloxazolyl group, methylbenzoxazolyl group, chloroethenyl group, bromoethenyl group, chloropropenyl group, chlorohexenyl group, methylcyclopropyl group, ethylcyclopropyl group, chlorocyclopropyl group, methoxycyclopropyl group, methylcyclopentyl group, chlorohexyl group, methylcyclohexyl group, methylcyclopentenyl group, chlorocyclohexenyl group, methylcyclohexenyl group, N-methylpyrrolidyl group, N-ethylpyrrolidyl group and the like.

In the above formula (1), $R^5$ is a heteroaryl group having 3 to 8 ring member carbon atoms and 1 to 2 hetero atoms selected from the group consisting of oxygen atom, sulfur atom and nitrogen atom, an aryl group having 6 to 14 carbon atoms or an alkyl group having 1 to 12 carbon atoms.

All of these groups represented by $R^5$ may be substituted by at least one substituent selected from the group consisting of an alkyl group having 1 to 3 carbon atoms, a halogen atom, an alkoxyl group having 1 to 3 carbon atoms, an alkylthio group having 1 to 3 carbon atoms, cyano group, nitro group and amino group. Illustrative examples of the substituent are the same as those listed for $R^1$.

Illustrative examples of the substituted and unsubstituted heteroaryl groups, substituted and unsubstituted aryl groups and substituted and unsubstituted alkyl groups are the same as those listed for $R^4$.

There are various positional isomers of compounds having the above groups in many cases, and all of the isomers can be used in the present invention without restriction. For example, when the group is a methylphenyl group, it may be either one of o-methylphenyl group, m-methylphenyl group and p-methylphenyl group. When the group is a butyl group, it may be either one of n-butyl group, s-butyl group and t-butyl group.

Preferred examples of the ethenylamide compound of formula 1 include 2-chloro-N-(2,6-dimethylphenyl)-N-(1-phenylethenyl)acetamide (Compound No. 1 of Example which will be described later, and hereinafter numerals in parentheses after the compound indicate the compound numbers of Examples), 2-chloro-N-(2-methoxyethyl)-N-(2-methyl-1-phenyl-1-propenyl)acetamide (No. 2), 2-chloro-N-(2-ethoxyethyl)-N-(1-phenyl-1-propenyl)acetamide (No. 3), 2-chloro-N-(2-ethoxyethyl)-N-(2-methyl-1-phenyl-1-propenyl)acetamide (No. 4), N-(3-methoxypropyl)-N-(2-methyl-1-(4-methylphenyl)-1-propenyl)acetamide (No. 5), 2-bromo-N-pentyl-N-(1-(3-chlorophenyl)ethenyl)-acetamide (No. 6), 2-methyl-N-(3-ethoxypropyl)-N-(2-methyl-1-(4-methoxyphenyl)-1-propenyl)propylamide (No. 7), 2-chloro-N-phenyl-N-(2-methyl-1-(4-methylthiophenyl-1-butenyl)acetamide (No. 8), N-(3-propoxypropyl)-N-(2-methyl-1-(4-cyanophenyl)-1-propenyl)benzamide (No. 9), 4-ethyl-N-(2-thienyl)-N-(1-(1-naphthyl)-1-butenyl)benzamide (No. 10), 4-methoxy-N-ethyl-N-(2-methyl-1-(2-pyridyl)-1-propenyl)benzamide (No. 11), 2-methoxy-N-butyl-N-(2-methyl-1-(2-thienyl)-1-propenyl)acetamide (No. 12), 2-chloro-N-(2-(4-methoxythienyl))-N-(2-methyl-1-(2-furyl)-1-propenyl)acetamide (No. 13), 2-chloro-N-(2,4-dichlorophenyl)-N-(1-phenylethenyl)acetamide (No. 14), 2-bromo-N-methoxymethyl-N-(1-(2,4-dimethylphenyl)-1-propenyl)acetamide (No. 15), 2-chloro-N-(2,6-dimethylphenyl)-N-(1-(N-methylpyrimidinyl)ethenyl)-acetamide (No. 16), N-(1-naphthyl)-N-(2-methyl-1-(4-bromophenyl)-1-propenyl)propylamide (No. 17), 2,2,2-trifluoro-N-(2-methylthioethyl)-N-(1-(4-isopropylphenyl)-1-pentenyl)acetamide (No. 18), N-(2-ethoxycarbonylethyl)-N-(1-(2-(4-methoxythionyl))-ethenyl)benzamide (No. 19), N-ethyl-N-(1-(4-nitrophenyl)-2-cyclohexylethenyl) thiazoamide (No. 20) and the like.

Out of the ethenylamide compounds of formula 1, from the viewpoint of herbicidal activity, more preferred are ethenylamide compounds in which $R^1$ is a unsubstituted heteroaryl group having 3 to 8 carbon atoms and 1 to 2 hetero atoms selected from the group consisting of oxygen atom, sulfur atom and nitrogen atom, unsubstituted aryl group having 6 to 14 carbon atoms, or substituted heteroaryl group or substituted aryl group obtained by substituting at least one hydrogen atom of the unsubstituted heteroaryl group or the unsubstituted aryl group by a substituent selected from the group consisting of an alkyl group having 1 to 3 carbon atoms, a halogen atom, an alkoxyl group having 1 to 3 carbon atoms, an alkylthio group having 1 to 3 carbon atoms, cyano group, nitro group and amino group, respectively; $R^2$ and $R^3$ are independently hydrogen atom or an alkyl group having 1 to 12 carbon atoms, or are bonded together with the carbon atom, to which $R^2$ and $R^3$ are bonded, to form a ring having 5 to 6 carbon atoms; $R^4$ is an unsubstituted alkyl group having 1 to 12 carbon atoms, unsubstituted alkenyl group having 2 to 12 carbon atoms, unsubstituted alkynyl group having 2 to 12 carbon atoms, unsubstituted aryl group having 6 to 14 carbon atoms, unsubstituted heteroaryl group having 3 to 8 carbon atoms, unsubstituted cycloalkyl group having 3 to 6 carbon atoms, unsubstituted cycloalkenyl group having 4 to 6 carbon atoms, unsubstituted heterocycloalkyl group having 4 to 5 carbon atoms, or substituted alkyl group, substituted alkenyl group, substituted alkynyl group, substituted heteroaryl group, substituted cycloalkyl group or substituted heterocycloalkyl group obtained by substituting at least one hydrogen atom of the unsubstituted alkyl group, unsubstituted alkenyl group, unsubstituted alkynyl group, unsubstituted heteroaryl group, unsubstituted cycloalkyl group or unsubstituted heterocycloalkyl group by a substituent selected from the group consisting of an alkyl group having 1 to 3 carbon atoms, a halogen atom, an alkoxyl group having 1 to 3 carbon atoms, an alkylthio group having 1 to 3 carbon atoms, cyano group, nitro group and amino group, respectively, (provided that when the hydrogen atom of the unsubstituted alkyl group or the unsubstituted alkenyl group is substituted, the substituent cannot be an alkyl group having 1 to 3 carbon atoms); and $R^5$ is a monochloromethyl group.

Further, from the viewpoint that the safening effect of the ethenylamide compound is large when they are used in combination with a dichloroacetamide compound represented by formula (2) or (3) as a safener which will be detailed hereinafter, out of the ethenylamide compounds of formula 1, particularly preferred are ethenylamide compounds in which $R^1$ is an unsubstituted aryl group having 6 to 14 carbon atoms or substituted aryl group obtained by substituting at least one hydrogen atom of the unsubstituted aryl group by a substituent selected from the group consisting of an alkyl group having 1 to 3 carbon atoms, a halogen atom, an alkoxyl group having 1 to 3 carbon atoms, an alkylthio group having 1 to 3 carbon atoms, cyano group, nitro group and amino group; $R^2$ and $R^3$ are independently hydrogen atom or an alkyl group having 1 to 12 carbon atoms, or are bonded together with the carbon atom, to which $R^2$ and $R^3$ are bonded, to form a ring having 5 to 6 carbon atoms; $R^4$ is an unsubstituted alkyl group having 1 to 12 carbon atoms, unsubstituted alkenyl group having 2 to 12 carbon atoms, unsubstituted alkynyl group having 2 to 12 carbon atoms, unsubstituted aryl group having 6 to 14 carbon atoms, unsubstituted heteroaryl group having 3 to 8 carbon atoms, unsubstituted cycloalkyl group having 3 to 6 carbon atoms, unsubstituted cycloalkenyl group having 4 to 6 carbon atoms, unsubstituted heterocycloalkyl group having 4 to 5 carbon atoms, or substituted alkyl group, substituted alkenyl group, substituted alkynyl group, substituted heteroaryl group, substituted cycloalkyl group or substituted heterocycloalkyl group obtained by substituting at least one hydrogen atom of the unsubstituted alkyl group, unsubstituted alkenyl group, unsubstituted alkynyl group, unsubstituted heteroaryl group, unsubstituted cycloalkyl group or unsubstituted heterocycloalkyl group by a substituent selected from the group consisting of alkyl group having 1 to 3 carbon atoms, halogen atom, alkoxyl group having 1 to 3 carbon atoms, alkylthio group having 1 to 3 carbon atoms, cyano group, nitro group and amino group, respectively, (when the hydrogen atom of the unsubstituted alkyl group or the unsubstituted alkenyl group is substituted, the substituent cannot be an alkyl group having 1 to 3 carbon atoms), respectively; and $R^5$ is a monochloromethyl group.

The herbicidal composition of the present invention comprises a dichloroacetamide safener in addition to an ethenylamide compound of the above formula 1 as a herbicidally effective component.

Any dichloroacetamide compounds which are known as a safener showing the effect of safening the herbicidally effective component of a herbicide can be used as the dichloroacetamide safener used in the present invention. The safening effect means the effect of protecting cultivated crops by reducing or eliminating phytotoxicity without influencing the herbicidal effect of a herbicidally effective component, that is, "the killing (herbicidal) effect on weeds to be removed". Therefore, the term "safener" as used herein denotes a concept comprehending counter-agents and antidotes.

Examples of the dichloroacetamide safener include compounds in which a nitrogen atom constituting an amide bond forms a hetero ring. Out of the dichloroacetamide safeners, preferred are a compound represented by the following formula (2):

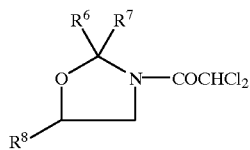

(2)

wherein $R^6$ and $R^7$ are independently hydrogen atom or an alkyl group having 1 to 3 carbon atoms; and
$R^8$ is a heteroaryl group having 3 to 8 ring member carbon atoms and 1 to 2 hetero atoms selected from the group consisting of oxygen atom, sulfur atom and nitrogen atom, an alkyl group having 1 to 3 carbon atoms or hydrogen atom, and the heteroaryl group may be substituted by at least one substituent selected from the group consisting of an alkyl group having 1 to 3 carbon atoms, a halogen atom, an alkoxyl group having 1 to 3 carbon atoms, an alkylthio group having 1 to 3 carbon atoms, cyano group, nitro group and amino group, or a compound represented by the following formula (3):

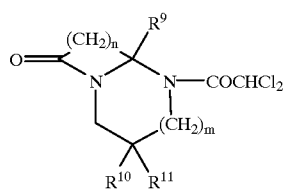

(3)

wherein $R^9$, $R^{10}$ and $R^{11}$ are independently a hydrogen atom or an alkyl group having 1 to 2 carbon atoms, n is 2 or 3, and m is 0 or 1,
because they have a high effect of safening the herbicidally effective component of the ethenylamide compound of the above formula 1 and a low adverse influence on herbicidal effect.

In the above formula (2), $R^6$ and $R^7$ are independently hydrogen atom or an alkyl group having 1 to 3 carbon atoms. Illustrative examples of the alkyl group include methyl group, ethyl group, n-propyl group, i-propyl group and the like.

In the above formula (2), $R^8$ is a heteroaryl group having 3 to 8 ring member carbon atoms and 1 to 2 hetero atoms selected from the group consisting of oxygen atom, sulfur atom and nitrogen atom, an alkyl group having 1 to 3 carbon atoms or hydrogen atom. Illustrative examples of the alkyl group are the same as those listed for $R^6$ and $R^7$ and illustrative examples of the substituted and unsubstituted heteroaryl groups are the same as those listed for $R^1$.

Preferred examples of the dichloroacetamide compound represented by the above formula (2) include 2,2,5-trimethyl-3-dichloroacetyloxazolidine (Compound A of Example which will be described later, and hereinafter, reference symbols in parentheses indicate compound reference symbols of Examples), 2,2-dimethyl-3-dichloroacetyloxazolidine (B), 2-ethyl-2-methyl-3-dichloroacetyloxazolidine (C), 2,2-dimethyl-5-(2-furyl)-3-dichloroacetyloxazolidine (D), 2-methyl-5-(2-(4-methylfuryl))-3-dichlorooxazolidine (E) and the like.

In the above formula (3), $R^9$, $R^{10}$ and $R^{11}$ are independently hydrogen atom or an alkyl group having 1 to 2 carbon atoms. Illustrative examples of the alkyl group include methyl group and ethyl group.

Preferred examples of the dichloroacetamide compound represented by the above formula (3) include 4-dichloroacetyl-5-methyl-9-oxo-1,4-diazabicyclo[3.4.0]nonane (Compound F of Example which will be described later and hereinafter, reference symbols in parentheses indicate compound reference symbols of Examples), 5-dichloroacetyl-3,3,6-trimethyl-9-oxo-1,5-diazabicyclo[4.3.0]nonane (G), 4-dichloroacetyl-9-oxo-1,5-diazabicyclo[3.4.0]nonane (H), 5-dichloroacetyl-6-ethyl-9-oxo-1,5-diazabicyclo[4.3.0]nonane (I), 5-dichloroacetyl-3,3,6-trimethyl-10-oxo-1,5-azabicyclo[4.4.0]decane (J) and the like.

The dichloroacetamide compounds represented by the above formula (2) and (3) have an especially large effect of protecting cultivated crops against the ethenylamide compound of formula 1. Therefore, these compounds can be used in combination with the ethenylamide compound of formula 1 as a herbicidal composition, and functions as a safener for a herbicide comprising the ethenylamide compound of formula 1 even when it is used at a time different from application time of the ethenylamide compound of formula 1. That is, the compound can be used for the pretreatment of seeds or seedling (direct application to seeds or trimmed branches) or applied in the soil before or after sowing, before use of the herbicide comprising the ethenylamide compound of formula 1.

In the herbicidal composition of the present invention, the blending ratio of the ethenylamide compound of formula 1 as a herbicidally effective component to a dichloroacetamide safener is not particularly limited and may be suitably determined according to cultivation environment such as crops and soil.

The ethenylamide compound of formula 1 is contained in a herbicidally effective amount, and the dichloroacetamide compound is preferably contained in an amount of 0.01 to 1 part by weight, more preferably 0.02 to 0.5 part by weight, particularly preferably 0.025 to 0.25 part by weight based on one part by weight of the ethenylamide compound of formula 1.

The herbicidal composition of the present invention is basically composed of a mixture of the ethenylamide compound of formula 1 and the dichloroacetamide safener. This mixture may be used as it is or mixed with a solid or liquid carrier or with other adjuvant as required to make preparations. The form of the preparations is not particularly limited, and conventionally known preparation forms are employed. For example, the preparations may be made in a form of dust, coarse granules, fine granules, granules, wettable powder, emulsion, flowables, oil suspension or the like.

Any conventionally known solid carrier may be used without restriction as the solid carrier which can be used to make the preparations of the herbicidal composition of the present invention. Illustrative examples of the solid carrier advantageously used in the present invention include clays typified by kaolinite, montmorillonite, attapulgite and zieclite; inorganic substances such as talc, mica, pyrophyllite, pumice, vermiculite, gypsum, calcium carbonate, dolomite, magnesium diatomaceous earth, lime, phosphorus lime, zeolite, silisic anhydride and synthetic calcium silicate; vegetable organic substances such as soybean flour, tobacco powder, walnut powder, wheat flour, wood dust, starch and crystalline cellulose; synthetic and natural polymer compounds such as coumarone resin, petroleum resin, alkyd resin, polyvinyl chloride, polyalkylene glycol, ketone resin, ester gum, copal gum and dammar gum; waxes such as carnauba wax and beeswax; urea; and the like.

Any conventional liquid carrier may be used without restriction as the liquid carrier which can be used to make the preparations of the herbicidal composition of the present invention. Preferred examples of the liquid carrier include paraffin-based and naphthene-based hydrocarbons such as kerosene, mineral oil, spindle oil and white oil; aromatic hydrocarbons such as benzene, toluene, xylene, ethylbenzene, cumene and methylnaphthalene; chlorine-based hydrocarbons such as carbon tetrachloride, chloroform, trichloroethylene, monochlorobenzene and o-chlorotoluene; ethers such as dioxane and tetrahydrofuran; ketones such as acetone, methylethyl ketone, diisobutyl ketone, cyclohexanone, acetophenone and isophorone; esters such as ethyl acetate, amyl acetate, ethylene glycol acetate, diethylene glycol acetate, dibutyl maleate and diethyl succinate; alcohols such as methanol, n-hexanol, ethylene glycol and diethylene glycol; ether alcohols such as ethylene glycol phenyl ether, diethylene glycol ethyl ether and ethylene glycol butyl ether; polar solvents such as dimethyl formamide and dimethyl sulfoxide; water; and the like.

In making preparations, any conventionally known surfactant may be used without restriction for the purpose of emulsification, dispersion, wetting, diffusion, bonding, the control of degradation, the stabilization of an effective component, the improvement of flowability, rust prevention and the like. The surfactant may be nonionic, cationic, anionic or amphoteric, but generally nonionic and/or anionic. Preferred examples of the nonionic surfactant include addition products of higher alcohols such as lauryl alcohol, stearyl alcohol and oleic alcohol with ethylene oxide; addition products of alkyl phenols such as isooctylphenol and nonylphenol with ethylene oxide; addition products of alkyl naphthols such as butyl naphthol and octyl naphthol with ethylene oxide; addition products of higher fatty acids such as palmitic acid, stearic acid and oleic acid with ethylene oxide; addition products of stearyl phosphoric acid, dilauryl phosphoric acid and dialkyl phoshoric acid with ethylene oxide; addition products of amines such as dodecylamine and acid amides such as stearic acid amide with ethylene oxide; addition products of higher fatty acid esters of polyhydric alcohol such as sorbitan with ethylene oxide; addition products of ethylene oxide with propylene oxide; esters between polyvalent fatty acids such as dioctyl succinate and alcohols; and the like. Preferred examples of the anionic surfactant include alkyl sulfates such as sodium lauryl sulfate and amine salt of oleic alcohol sulfate; alkyl sulfonates such as sodium salt of dioctyl sulfosuccinate and sodium 2-ethylhexene sulfonate; aryl sulfonates such as sodium i-propylnaphthalene sulfonate, sodium methylene bisnaphthalene sulfonate, sodium lignin sulfonate and sodium dodecylbenzene sulfonate; phosphates such as sodium tripolyphosphate; and the like.

At the time of making preparations, any conventionally known adjuvant may be used without restriction. The adjuvant is used for various purposes. The adjuvant is used when the herbicidal effect is enhanced by improving the degradation of a granular preparation. Preferred examples of the adjuvant include polymer compounds such as casein, gelatin, albumin, glue, sodium alginate, carboxyl methyl cellulose, methyl cellulose, hydroxyethyl cellulose and polyvinyl alcohol.

The above carrier, surfactant and adjuvant may be used alone or in combination according to purpose in view of the type of a preparation, the place of use and the like.

Method of making preparations in the present invention are not particularly limited and conventionally known methods are used.

For example, to prepare a wettable powder, the ethenylamide compound of formula 1 and a dichloroacetamide safener are dissolved in an organic solvent, a surfactant and a carrier are added to the resulting solution, milled and mixed, and the organic solvent is removed to obtain a wettable powder.

Further, to prepare an emulsion, the ethenylamide compound of formula 1, a dichloroacetamide safener and a surfactant are mixed into a petroleum solvent such as xylene to obtain an emulsion.

Moreover, to prepare granules, the ethenylamide compound of formula 1, a dichloroacetamide safener, a carrier, a surfactant and water are kneaded fully, and the resulting mixture is extruded to a predetermined grain size and dried to obtain granules.

The herbicidal composition of the present invention is generally used in an amount of 2 to 5,000 g, preferably 10 to 2,000 g per 1 ha. in terms of the ethenylamide compound of formula 1. The time of using the herbicidal composition of the present invention to exhibit its effect is any time from before the germination of weeds to the early stage of growth and the usable period is very long. Further, the herbicidal composition of the present invention can weed out both weeds before and after germination by one time of use.

The following examples are provided for the purpose of further illustrating the present invention but are in no way to be taken as limiting.

In the following Preparation Examples and Examples, Compounds No. 1 to 20 shown in Table 1 were used as the ethenylamide compound of formula 1 and Compounds A to J shown in Tables 2 and 3 were used as the dichloroacetamide safener.

TABLE 1
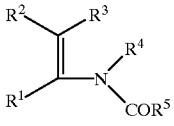
| No | R¹ | R² | R³ | R⁴ | R⁵ |
|---|---|---|---|---|---|
| 1 | 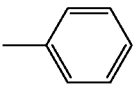 | H | H | 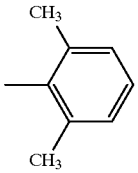 | $CH_2Cl$ |
| 2 | 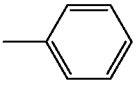 | $CH_3$ | $CH_3$ | $CH_2CH_2OCH_3$ | $CH_2Cl$ |
| 3 | 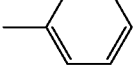 | H | $CH_3$ | $CH_2CH_2OC_2H_5$ | $CH_2Cl$ |
| 4 | 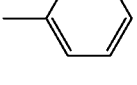 | $CH_3$ | $CH_3$ | $CH_2CH_2OC_2H_5$ | $CH_2Cl$ |
| 5 | 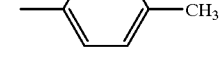 | $CH_3$ | $CH_3$ | $(CH_2)_3OCH_3$ | $CH_3$ |
| 6 | 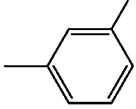 | H | H | $(CH_2)_4CH_3$ | $CH_2Br$ |
| 7 | 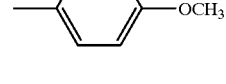 | $CH_3$ | $CH_3$ | $(CH_2)_3OC_2H_5$ | $CH(CH_3)_2$ |
| 8 | 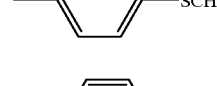 | $CH_3$ | $C_2H_5$ | 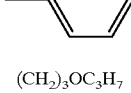 | $CH_2Cl$ |
| 9 | 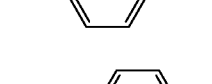 | $CH_3$ | $CH_3$ | $(CH_2)_3OC_3H_7$ | 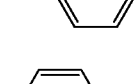 |
| 10 | 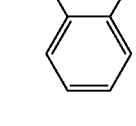 | $C_2H_5$ | H | 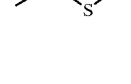 | 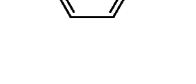 |
| 11 | 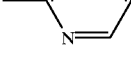 | $CH_3$ | $CH_3$ | $C_2H_5$ | 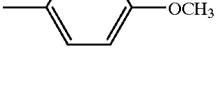 |

TABLE 1-continued
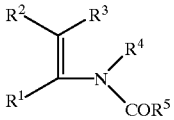
| No | R¹ | R² | R³ | R⁴ | R⁵ |
|----|----|----|----|----|----|
| 12 | 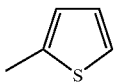 | CH₃ | CH₃ | (CH₂)₃CH₃ | CH₂OCH₃ |
| 13 | 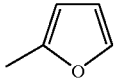 | CH₃ | CH₃ | 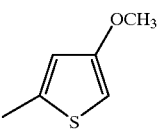 | CH₂Cl |
| 14 | 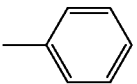 | H | H | 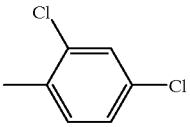 | CH₂Cl |
| 15 | 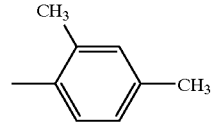 | CH₃ | H | CH₂OCH₃ | CH₂Br |
| 16 | 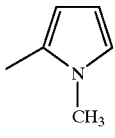 | H | H | 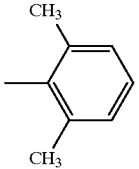 | CH₂Cl |
| 17 |  | CH₃ | CH₃ | 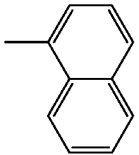 | C₂H₅ |
| 18 | 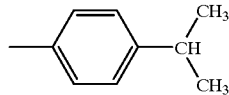 | H | C₃H₇ | (CH₂)₂SCH₃ | CF₃ |
| 19 | 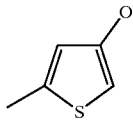 | H | H | C₂H₄CO₂C₂H₅ | 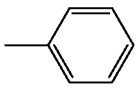 |
| 20 | 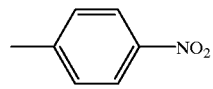 | —(CH₂)₅— | | C₂H₅ | 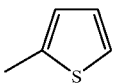 |

TABLE 2

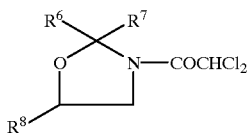

| Reference letter | $R^6$ | $R^7$ | $R^8$ |
|---|---|---|---|
| A | $CH_3$ | $CH_3$ | $CH_3$ |
| B | $CH_3$ | $CH_3$ | H |
| C | $C_2H_5$ | $CH_3$ | H |
| D | $CH_3$ | $CH_3$ | ![2-furyl] |
| E | H | $CH_3$ | ![2,5-dimethylfuryl] |

TABLE 3

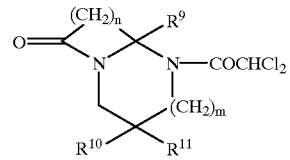

| Reference letter | $R^9$ | $R^{10}$ | $R^{11}$ | n | m |
|---|---|---|---|---|---|
| F | $CH_3$ | H | H | 3 | 0 |
| G | $CH_3$ | $CH_3$ | $CH_3$ | 2 | 1 |
| H | H | H | H | 3 | 0 |
| I | $C_2H_5$ | H | H | 2 | 1 |
| J | $CH_3$ | $CH_3$ | $CH_3$ | 3 | 1 |

PREPARATION EXAMPLES 1 TO 28

60 parts by weight of ethenylamide compound No. 1 shown in Table 1, 3 parts by weight of dichloroacetamide safener A and 15 parts by weight of the SM100 surfactant (trade name of Toho Chemical Industry Co., Ltd.) were well mixed with 22 parts by weight of xylene to prepare an emulsion of a herbicidal composition (Preparation Example 1). The emulsions of herbicidal compositions of Preparation Examples 2 to 28 were prepared from components shown in Table 4 in the same manner as described above.

TABLE 4

| Pre. Ex. No. | Herbicidal effective component (parts by weight) | Safener (parts by weight) | Solvent (parts by weight) | Surfactant (parts by weight) |
|---|---|---|---|---|
| 1 | No. 1 60 | A 3 | Xylene 22 | SM100 15 |
| 2 | No. 1 60 | C 3 | Xylene 22 | SM100 15 |
| 3 | No. 1 60 | F 3 | Xylene 22 | SM100 15 |
| 4 | No. 1 60 | H 3 | Xylene 22 | SM100 15 |
| 5 | No. 2 60 | B 3 | Xylene 22 | SM100 15 |
| 6 | No. 2 60 | D 3 | Xylene 22 | SM100 15 |
| 7 | No. 2 60 | G 3 | Xylene 22 | SM100 15 |
| 8 | No. 2 60 | I 3 | Xylene 22 | SM100 15 |
| 9 | No. 3 60 | B 3 | Xylene 22 | SM100 15 |
| 10 | No. 3 60 | E 3 | Xylene 22 | SM100 15 |
| 11 | No. 3 60 | I 3 | Xylene 22 | SM100 15 |
| 12 | No. 3 60 | J 3 | Xylene 22 | SM100 15 |
| 13 | No. 4 60 | A 3 | Xylene 22 | SM100 15 |
| 14 | No. 4 60 | B 3 | Xylene 22 | SM100 15 |
| 15 | No. 4 60 | F 3 | Xylene 22 | SM100 15 |
| 16 | No. 4 60 | G 3 | Xylene 22 | SM100 15 |
| 17 | No. 10 60 | C 3 | Xylene 22 | SM100 15 |
| 18 | No. 10 60 | E 3 | Xylene 22 | SM100 15 |

TABLE 4-continued

| Pre. Ex. No. | Herbicidal effective component (parts by weight) | Safener (parts by weight) | Solvent (parts by weight) | Surfactant (parts by weight) |
|---|---|---|---|---|
| 19 | No. 10<br>60 | H<br>3 | Xylene<br>22 | SM100<br>15 |
| 20 | No. 10<br>60 | J<br>3 | Xylene<br>22 | SM100<br>15 |
| 21 | No. 15<br>60 | C<br>3 | Xylene<br>22 | SM100<br>15 |
| 22 | No. 15<br>60 | D<br>3 | Xylene<br>22 | SM100<br>15 |
| 23 | No. 15<br>60 | H<br>3 | Xylene<br>22 | SM100<br>15 |
| 24 | No. 15<br>60 | I<br>3 | Xylene<br>22 | SM100<br>15 |
| 25 | No. 18<br>60 | D<br>3 | Xylene<br>22 | SM100<br>15 |
| 26 | No. 18<br>60 | E<br>3 | Xylene<br>22 | SM100<br>15 |
| 27 | No. 18<br>60 | F<br>3 | Xylene<br>22 | SM100<br>15 |
| 28 | No. 18<br>60 | H<br>3 | Xylene<br>22 | SM100<br>15 |

Pre. Ex. = Preparation Example

EXAMPLES 1 to 28

The herbicidal activity of each of the herbicidal compositions prepared in the above Preparation Examples and phytotoxicity of each of the herbicidal compositions were evaluated as follows. That is, a plastic container (having 35 cm in length, 18 cm in width×14 cm in height) was filled with the upland farm soil, corn seeds were sown in the soil to a depth of 3 cm, and the seeds of barnyardgrass, southern crabgrass, annual bluegrass, common lamb's-quarters and hairy galinsoga were sown in the soil to a depth of 0.5 to 1 cm. After these seeds were covered with soil, a herbicidal composition to be tested was sprayed over the surface of the soil so as to be an amount of 1,500 g per 1 ha. in terms of the ethenylamide compound (herbicidally effective component) (75 g of a dichloroacetamide safener per 1 ha.).

In the spray treatment, an emulsion used was prepared by adding 99.875 parts by weight of water to 0.125 part by weight of each herbicidal composition (emulsion) to be sprayed. After the above treatment, the seeds were allowed to grow in a greenhouse heated at an average temperature of 25° C. and the herbicidal effect of each composition was checked after 2 weeks. The results are shown in Table 5. The evaluation of phytotoxic action to crops and the standards of the herbicidal effect were shown in six levels from level 0 to level 5. That is, level 5 is a weed killing rate of 100% (complete death), level 4 is a weed killing rate of 99 to 75.3%, level 3 a weed killing rate of 74 to 50%, level 2 a weed killing rate of 49 to 25%, level 1 a weed killing rate of 24 to 1% and level 0 a weed killing rate of 0% (no effect). As a control to be used is crops treated with a herbicide only (no use of safener) and crops untreated with a herbicide.

TABLE 5

| Ex. No. | Herbicide Preparations No. | Herbicidal activity | | | | | Phytotoxicity Corn |
|---|---|---|---|---|---|---|---|
| | | Southern Crabgrass | Annual bluegrass | Barnyard-grass | Common lamb's-quarters | Hairy galinsoga | |
| 1 | 1 | 5 | 5 | 5 | 4 | 4 | 0 |
| 2 | 2 | 5 | 4 | 5 | 4 | 3 | 0 |
| 3 | 3 | 5 | 4 | 4 | 4 | 3 | 0 |
| 4 | 4 | 5 | 5 | 4 | 4 | 4 | 0 |
| 5 | 5 | 4 | 5 | 4 | 4 | 4 | 0 |
| 6 | 6 | 5 | 5 | 4 | 4 | 4 | 0 |
| 7 | 7 | 5 | 5 | 5 | 4 | 3 | 0 |
| 8 | 8 | 5 | 5 | 5 | 4 | 3 | 0 |
| 9 | 9 | 4 | 5 | 4 | 4 | 3 | 0 |
| 10 | 10 | 4 | 5 | 4 | 4 | 3 | 0 |
| 11 | 11 | 5 | 4 | 4 | 4 | 4 | 0 |
| 12 | 12 | 5 | 5 | 4 | 4 | 4 | 0 |
| 13 | 13 | 5 | 5 | 5 | 4 | 4 | 0 |
| 14 | 14 | 5 | 5 | 5 | 4 | 4 | 0 |
| 15 | 15 | 5 | 5 | 5 | 4 | 4 | 0 |
| 16 | 16 | 5 | 5 | 4 | 4 | 4 | 0 |
| 17 | 17 | 4 | 5 | 4 | 4 | 3 | 0 |
| 18 | 18 | 4 | 5 | 4 | 4 | 3 | 0 |
| 19 | 19 | 5 | 5 | 4 | 4 | 4 | 0 |
| 20 | 20 | 5 | 5 | 4 | 4 | 4 | 0 |
| 21 | 21 | 5 | 4 | 4 | 4 | 4 | 0 |
| 22 | 22 | 5 | 4 | 4 | 4 | 4 | 0 |
| 23 | 23 | 4 | 5 | 4 | 4 | 3 | 0 |

TABLE 5-continued

| | Herbicide | Herbicidal activity | | | | | |
|---|---|---|---|---|---|---|---|
| Ex. No. | Preparations No. | Southern Crabgrass | Annual bluegrass | Barnyard-grass | Common lamb's-quarters | Hairy galinsoga | Phytotoxicity Corn |
| 24 | 24 | 4 | 5 | 5 | 4 | 3 | 0 |
| 25 | 25 | 4 | 5 | 4 | 4 | 4 | 0 |
| 26 | 26 | 5 | 5 | 4 | 4 | 4 | 0 |
| 27 | 27 | 5 | 5 | 5 | 4 | 4 | 0 |
| 28 | 28 | 5 | 5 | 5 | 4 | 4 | 0 |

Ex. = Example

PREPARATION EXAMPLES 29 to 56

60 parts by weight of ethenylamide compound No. 1 shown in Table 1 and 15 parts by weight of the SM100 surfactant were well mixed with 25 parts by weight of xylene to prepare emulsion A containing only a herbicidally effective component and 5 parts by weight of dichloroacetamide safener A shown in Table 2 and 15 parts by weight of the SM 100 surfactant were well mixed with 80 parts by weight of xylene to prepare emulsion B containing only a safener (Preparation Example 29).

Emulsions A and B of Preparation Examples 30 to 56 were prepared from components shown in Table 6 in the same manner as described above.

TABLE 6

| | Emulsion A | | | Emulsion B | | |
|---|---|---|---|---|---|---|
| Pre. Ex. No. | Herbicidally effective component (parts by weight) | Solvent (parts by weight) | Surfactant (parts by weight) | Safener (parts by weight) | Solvent (parts by weight) | Surfactant (parts by weight) |
| 29 | No. 1 60 | Xylene 25 | SM100 15 | A 5 | Xylene 80 | SM100 15 |
| 30 | No. 1 60 | Xylene 25 | SM100 15 | C 5 | Xylene 80 | SM100 15 |
| 31 | No. 1 60 | Xylene 25 | SM100 15 | F 5 | Xylene 80 | SM100 15 |
| 32 | No. 1 60 | Xylene 25 | SM100 15 | H 5 | Xylene 80 | SM100 15 |
| 33 | No. 2 60 | Xylene 25 | SM100 15 | B 5 | Xylene 80 | SM100 15 |
| 34 | No. 2 60 | Xylene 25 | SM100 15 | D 5 | Xylene 80 | SM100 15 |
| 35 | No. 2 60 | Xylene 25 | SM100 15 | G 5 | Xylene 80 | SM100 15 |
| 36 | No. 2 60 | Xylene 25 | SM100 15 | I 5 | Xylene 80 | SM100 15 |
| 37 | No. 3 60 | Xylene 25 | SM100 15 | B 5 | Xylene 80 | SM100 15 |
| 38 | No. 3 60 | Xylene 25 | SM100 15 | E 5 | Xylene 80 | SM100 15 |
| 39 | No. 3 60 | Xylene 25 | SM100 15 | I 5 | Xylene 80 | SM100 15 |
| 40 | No. 3 60 | Xylene 25 | SM100 15 | J 5 | Xylene 80 | SM100 15 |
| 41 | No. 4 60 | Xylene 25 | SM100 15 | A 5 | Xylene 80 | SM100 15 |
| 42 | No. 4 60 | Xylene 25 | SM100 15 | B 5 | Xylene 80 | SM100 15 |
| 43 | No. 4 60 | Xylene 25 | SM100 15 | F 5 | Xylene 80 | SM100 15 |
| 44 | No. 4 60 | Xylene 25 | SM100 15 | G 5 | Xylene 80 | SM100 15 |
| 45 | No. 10 60 | Xylene 25 | SM100 15 | C 5 | Xylene 80 | SM100 15 |
| 46 | No. 10 60 | Xylene 25 | SM100 15 | E 5 | Xylene 80 | SM100 15 |
| 47 | No. 10 60 | Xylene 25 | SM100 15 | H 5 | Xylene 80 | SM100 15 |
| 48 | No. 10 60 | Xylene 25 | SM100 15 | J 5 | Xylene 80 | SM100 15 |
| 49 | No. 15 60 | Xylene 25 | SM100 15 | C 5 | Xylene 80 | SM100 15 |
| 50 | No. 15 60 | Xylene 25 | SM100 15 | D 5 | Xylene 80 | SM100 15 |
| 51 | No. 15 | Xylene | SM100 | H | Xylene | SM100 |

TABLE 6-continued

| Pre. Ex. No. | Emulsion A | | | Emulsion B | | |
|---|---|---|---|---|---|---|
| | Herbicidally effective component (parts by weight) | Solvent (parts by weight) | Surfactant (parts by weight) | Safener (parts by weight) | Solvent (parts by weight) | Surfactant (parts by weight) |
| | 60 | 25 | 15 | 5 | 80 | 15 |
| 52 | No. 15 | Xylene | SM100 | I | Xylene | SM100 |
| | 60 | 25 | 15 | 5 | 80 | 15 |
| 53 | No. 18 | Xylene | SM100 | D | Xylene | SM100 |
| | 60 | 25 | 15 | 5 | 80 | 15 |
| 54 | No. 18 | Xylene | SM100 | E | Xylene | SM100 |
| | 60 | 25 | 15 | 5 | 80 | 15 |
| 55 | No. 18 | Xylene | SM100 | F | Xylene | SM100 |
| | 60 | 25 | 15 | 5 | 80 | 15 |
| 56 | No. 18 | Xylene | SM100 | H | Xylene | SM100 |
| | 60 | 25 | 15 | 5 | 80 | 15 |

EXAMPLES 29 to 56

The herbicidal activity and phytotoxicity of emulsion A containing a herbicidally effective component were evaluated using seeds covered with the effective component of emulsion B prepared from components shown in Table 6. In this operation, emulsion B was used as a neat solution, and 5 g of a dichloroacetamide compound based on 1 kg of seeds and 0.5% by weight of the seeds were used and shaken until the surface of each seed was uniformly covered with an effective component. The seeds treated as described above were sown as in the same manner as in Examples 1 to 28 and covered with soil, and then emulsion A prepared from components shown in Table 6 was sprayed over the soil so as to be an amount of 1,500 g per 1 ha in terms of the ethenylamide compound (herbicidally effective component). In the spray treatment, an emulsion used was prepared by adding 99.875 parts by weight of water to 0.125 part by weight of emulsion A to be sprayed. Evaluation was carried out in the same manner as in Examples 1 to 28. The results are shown in Table 7.

TABLE 7

| Ex. No. | Herbicide Preparations No. | Herbicidal activity | | | | | Phytotoxicity Corn |
|---|---|---|---|---|---|---|---|
| | | Southern crabgrass | Annual bluegrass | Barnyard-grass | Common lamb's-quarters | Hairy galinsoga | |
| 29 | 29 | 5 | 4 | 5 | 4 | 4 | 0 |
| 30 | 30 | 5 | 5 | 5 | 4 | 3 | 0 |
| 31 | 31 | 5 | 4 | 4 | 4 | 4 | 0 |
| 32 | 32 | 5 | 4 | 4 | 4 | 3 | 0 |
| 33 | 33 | 4 | 5 | 5 | 4 | 4 | 0 |
| 34 | 34 | 5 | 5 | 4 | 4 | 4 | 0 |
| 35 | 35 | 5 | 4 | 5 | 4 | 3 | 0 |
| 36 | 36 | 5 | 5 | 5 | 4 | 4 | 0 |
| 37 | 37 | 4 | 5 | 4 | 4 | 3 | 0 |
| 38 | 38 | 4 | 4 | 5 | 4 | 3 | 0 |
| 39 | 39 | 5 | 5 | 4 | 4 | 4 | 0 |
| 40 | 40 | 5 | 5 | 5 | 4 | 3 | 0 |
| 41 | 41 | 5 | 4 | 5 | 4 | 4 | 0 |
| 42 | 42 | 5 | 5 | 5 | 4 | 4 | 0 |
| 43 | 43 | 4 | 5 | 5 | 4 | 4 | 0 |
| 44 | 44 | 5 | 5 | 4 | 4 | 4 | 0 |
| 45 | 45 | 5 | 5 | 5 | 4 | 3 | 0 |
| 46 | 46 | 4 | 5 | 4 | 4 | 4 | 0 |
| 47 | 47 | 5 | 5 | 5 | 4 | 3 | 0 |
| 48 | 48 | 5 | 4 | 4 | 4 | 4 | 0 |
| 49 | 49 | 5 | 5 | 4 | 4 | 3 | 0 |
| 50 | 50 | 5 | 4 | 5 | 4 | 4 | 0 |
| 51 | 51 | 4 | 5 | 4 | 4 | 3 | 0 |
| 52 | 52 | 4 | 5 | 5 | 4 | 3 | 0 |
| 53 | 53 | 5 | 5 | 4 | 4 | 4 | 0 |
| 54 | 54 | 5 | 5 | 4 | 4 | 4 | 0 |
| 55 | 55 | 5 | 4 | 5 | 4 | 4 | 0 |
| 56 | 56 | 5 | 5 | 5 | 4 | 4 | 0 |

PREPARATION EXAMPLES 57 to 86

Herbicidal compositions were prepared in the same manner as in Preparation Examples 1 to 28 except compounds K to S shown in Table 8 were used as a safener.

TABLE 8

| Ref. letter | Comparative safener |
|---|---|
| K | 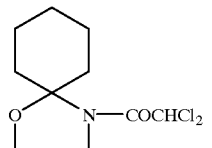 |
| L | 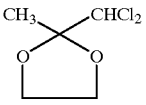 |
| M | 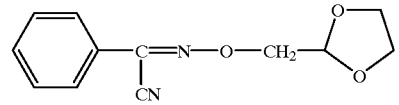 |
| N | 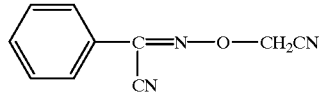 |
| O | 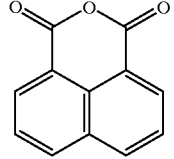 |
| P | 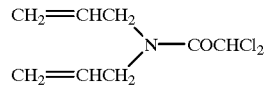 |

TABLE 8-continued

| Ref. letter | Comparative safener |
|---|---|
| Q | 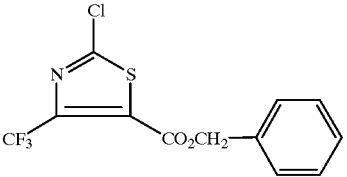 |
| R | 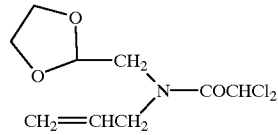 |
| S | 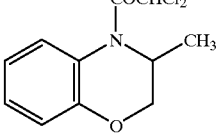 |

TABLE 9

| Preparation Example No. | Herbicidally effective component (parts by weight) | Safener (parts by weight) | Solvent (parts by weight) | Surfactant (parts by weight) |
|---|---|---|---|---|
| 57 | No. 1<br>60 | none | Xylene<br>25 | SM100<br>15 |
| 58 | No. 1<br>60 | K<br>3 | Xylene<br>22 | SM100<br>15 |
| 59 | No. 1<br>60 | L<br>3 | Xylene<br>22 | SM100<br>15 |
| 60 | No. 1<br>60 | M<br>3 | Xylene<br>22 | SM100<br>15 |
| 61 | No. 1<br>60 | N<br>3 | Xylene<br>22 | SM100<br>15 |
| 62 | No. 1<br>60 | O<br>3 | Xylene<br>22 | SM100<br>15 |
| 63 | No. 1<br>60 | P<br>3 | Xylene<br>22 | SM100<br>15 |
| 64 | No. 1<br>60 | Q<br>3 | Xylene<br>22 | SM100<br>15 |
| 65 | No. 1<br>60 | R<br>3 | Xylene<br>22 | SM100<br>15 |
| 66 | No. 1<br>60 | S<br>3 | Xylene<br>22 | SM100<br>15 |
| 67 | No. 4<br>60 | none | Xylene<br>25 | SM100<br>15 |
| 68 | No. 4<br>60 | K<br>3 | Xylene<br>22 | SM100<br>15 |
| 69 | No. 4<br>60 | L<br>3 | Xylene<br>22 | SM100<br>15 |

TABLE 9-continued

| Preparation Example No. | Herbicidally effective component (parts by weight) | Safener (parts by weight) | Solvent (parts by weight) | Surfactant (parts by weight) |
|---|---|---|---|---|
| 70 | No. 4 60 | M 3 | Xylene 22 | SM100 15 |
| 71 | No. 4 60 | N 3 | Xylene 22 | SM100 15 |
| 72 | No. 4 60 | O 3 | Xylene 22 | SM100 15 |
| 73 | No. 4 60 | P 3 | Xylene 22 | SM100 15 |
| 74 | No. 4 60 | Q 3 | Xylene 22 | SM100 15 |
| 75 | No. 4 60 | R 3 | Xylene 22 | SM100 15 |
| 76 | No. 4 60 | S 3 | Xylene 22 | SM100 15 |
| 77 | No. 18 60 | none | Xylene 25 | SM100 15 |
| 78 | No. 18 60 | K 3 | Xylene 22 | SM100 15 |
| 79 | No. 18 60 | L 3 | Xylene 22 | SM100 15 |
| 80 | No. 18 60 | M 3 | Xylene 22 | SM100 15 |
| 81 | No. 18 60 | N 3 | Xylene 22 | SM100 15 |
| 82 | No. 18 60 | O 3 | Xylene 22 | SM100 15 |
| 83 | No. 18 60 | P 3 | Xylene 22 | SM100 15 |
| 84 | No. 18 60 | Q 3 | Xylene 22 | SM100 15 |
| 85 | No. 18 60 | R 3 | Xylene 22 | SM100 15 |
| 86 | No. 18 60 | S 3 | Xylene 22 | SM100 15 |

COMPARATIVE EXAMLES 1 to 30

A treatment and evaluation were carried out in the same manner as in Examples 1 to 28 except that herbicidal compositions prepared in Preparation Examples 57 to 86 were used. The results are shown in Table 10.

TABLE 10

| | Herbicide | Herbicidal activity | | | | | |
|---|---|---|---|---|---|---|---|
| C. Ex. No. | Preparations No. | Southern crabgrass | Annual bluegrass | Barnyard-grass | Common lamb's-quarters | Hairy galinsoga | Phytotoxicity Corn |
| 1 | 57 | 5 | 5 | 5 | 4 | 4 | 3 |
| 2 | 58 | 5 | 5 | 4 | 4 | 3 | 3 |
| 3 | 59 | 5 | 5 | 4 | 4 | 4 | 3 |
| 4 | 60 | 5 | 5 | 4 | 4 | 4 | 3 |
| 5 | 61 | 5 | 5 | 5 | 4 | 4 | 3 |
| 6 | 62 | 5 | 5 | 4 | 4 | 4 | 3 |
| 7 | 63 | 5 | 5 | 5 | 4 | 4 | 2 |
| 8 | 64 | 5 | 4 | 5 | 4 | 4 | 3 |
| 9 | 65 | 5 | 4 | 5 | 4 | 4 | 3 |
| 10 | 66 | 5 | 5 | 5 | 4 | 4 | 2 |
| 11 | 67 | 5 | 5 | 5 | 4 | 4 | 3 |
| 12 | 68 | 5 | 5 | 5 | 4 | 4 | 3 |
| 13 | 69 | 5 | 5 | 5 | 4 | 4 | 3 |
| 14 | 70 | 5 | 4 | 5 | 4 | 4 | 3 |
| 15 | 71 | 5 | 4 | 5 | 4 | 4 | 3 |
| 16 | 72 | 5 | 5 | 5 | 4 | 3 | 3 |
| 17 | 73 | 5 | 5 | 5 | 4 | 4 | 2 |
| 18 | 74 | 5 | 5 | 4 | 4 | 4 | 3 |
| 19 | 75 | 5 | 5 | 5 | 4 | 4 | 2 |
| 20 | 76 | 5 | 5 | 4 | 4 | 3 | 2 |
| 21 | 77 | 5 | 4 | 4 | 4 | 4 | 3 |
| 22 | 78 | 5 | 4 | 4 | 4 | 4 | 3 |

TABLE 10-continued

|  | Herbicide | Herbicidal activity | | | | | |
|---|---|---|---|---|---|---|---|
| C. Ex. No. | Preparations No. | Southern crabgrass | Annual bluegrass | Barnyard-grass | Common lamb's-quarters | Hairy galinsoga | Phytotoxicity Corn |
| 23 | 79 | 5 | 4 | 4 | 4 | 4 | 3 |
| 24 | 80 | 5 | 4 | 4 | 4 | 3 | 3 |
| 25 | 81 | 5 | 4 | 4 | 4 | 4 | 3 |
| 26 | 82 | 5 | 4 | 4 | 4 | 4 | 3 |
| 27 | 83 | 5 | 4 | 4 | 4 | 4 | 2 |
| 28 | 84 | 5 | 4 | 4 | 4 | 3 | 3 |
| 29 | 85 | 5 | 4 | 4 | 4 | 4 | 3 |
| 30 | 86 | 5 | 4 | 4 | 4 | 4 | 2 |

C. Ex. = Comparative Example

When the herbicidal composition of the present invention is applied to broad-leaved crops such as soybeans, cotton and beet, and the crops of the grass family such as wheat, barley, corn and upland rice, it does not do phytotoxicity to cultivated crops and exhibits a marked herbicidal effect on many kinds of weeds.

What is claimed is:

1. A herbicidal composition comprising:

an ethenylamide compound represented by the following formula (1) as a herbicidally effective component:

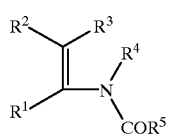

(1)

wherein $R^1$ is a heteroaryl group having 3 to 8 ring member carbon atoms and 1 to 2 hetero atoms selected from the group consisting of oxygen atom, sulfur atom and nitrogen atom, or aryl group having 6 to 14 carbon atoms, the heteroaryl group and the aryl group may be substituted by at least one substituent selected from the group consisting of an alkyl group having 1 to 3 carbon atoms, a halogen atom, an alkoxyl group having 1 to 3 carbon atoms, an alkylthio group having 1 to 3 carbon atoms, cyano group, nitro group and amino group; $R^2$ and $R^3$ are independently hydrogen atom or an alkyl group having 1 to 12 carbon atoms, or may be bonded together with the carbon atom, to which they are bonded, to form a ring having 5 to 6 ring member carbon atoms; $R^4$ is an alkyl group having 1 to 12 carbon atoms, an alkenyl group having 2 to 12 carbon atoms, an alkynyl group having 2 to 12 carbon atoms, an aryl group having 6 to 14 carbon atoms, a heteroaryl group having 3 to 8 carbon atoms, a cycloalkyl group having 3 to 6 carbon atoms, a cycloalkenyl group having 4 to 6 carbon atoms or a heterocycloalkyl group having 4 to 5 carbon atoms, all of these groups may be substituted by at least one substituent selected from the group consisting of an alkyl group having 1 to 3 carbon atoms, a halogen atom, an alkoxyl group having 1 to 3 carbon atoms, an alkylthio group having 1 to 3 carbon atoms, cyano group, nitro group and amino group, provided that when $R^4$ is an alkyl group having 1 to 12 carbon atoms or an alkenyl group having 2 to 12 carbon atoms, the substituent cannot be an alkyl group having 1 to 3 carbon atoms; and $R^5$ is a heteroaryl group having 3 to 8 ring member carbon atoms and 1 to 2 hetero atoms selected from the group consisting of oxygen atom, sulfur atom and nitrogen atom, an aryl group having 6 to 14 carbon atoms or an alkyl group having 1 to 12 carbon atoms, all of these groups may be substituted by at least one substituent selected from the group consisting of an alkyl group having 1 to 3 carbon atoms, a halogen atom, an alkoxyl group having 1 to 3 carbon atoms, an alkylthio group having 1 to 3 carbon atoms, cyano group, nitro group and amino group, provided that when $R^5$ is an alkyl group having 1 to 12 carbon atoms, the substituent cannot be an alkyl group having 1 to 3 carbon atoms; and a dichloroacetamide compound as a safener, wherein the dichloroacetamide compound is represented by the following formula (2):

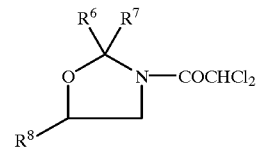

(2)

wherein $R^6$ and $R^7$ are independently a hydrogen atom or an alkyl group having 1 to 3 carbon atoms; and $R^8$ is a heteroaryl group having 3 to 8 ring member carbon atoms and 1 to 2 hetero atoms selected from the group consisting of oxygen atom, sulfur atom and nitrogen atom, an alkyl group having 1 to 3 carbon atoms or hydrogen atom, and the heteroaryl group may be substituted by at least one substituent selected from the group consisting of an alkyl group having 1 to 3 carbon atoms, a halogen atom, an alkoxyl group having 1 to 3 carbon atoms, an alkylthio group having 1 to 3 carbon atoms, cyano group, nitro group and amino group, or a compound represented by the following formula (3):

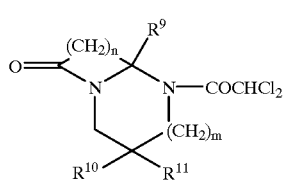

(3)

wherein $R^9$, $R^{10}$ and $R^{11}$ are independently a hydrogen atom or an alkyl group having 1 to 2 carbon atoms, n is 2 or 3, and m is 0 or 1.

2. The herbicidal composition of claim 1, wherein the dichloroacetamide compound is represented by the following formula (2):

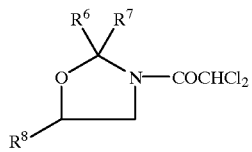

(2)

wherein $R^6$ and $R^7$ are independently a hydrogen atom or an alkyl group having 1 to 3 carbon atoms; and $R^8$ is a heteroaryl group having 3 to 8 ring member carbon atoms and 1 to 2 hetero atoms selected from the group consisting of oxygen atom, sulfur atom and nitrogen atom, an alkyl group having 1 to 3 carbon atoms or hydrogen atom, and the heteroaryl group may be substituted by at least one substituent selected from the group consisting of an alkyl group having 1 to 3 carbon atoms, halogen atom, alkoxyl group having 1 to 3 carbon atoms, an alkylthio group having 1 to 3 carbon atoms, cyano group, nitro group and amino group.

3. The herbicidal composition of claim 1, wherein the dichloroacetamide compound is represented by the following formula (3):

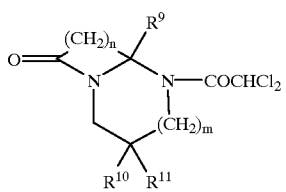

(3)

wherein $R^9$, $R^{10}$ and $R^{11}$ are independently a hydrogen atom or an alkyl group having 1 to 2 carbon atoms, n is 2 or 3, and m is 0 or 1.

4. A safener composition for a herbicidal composition comprising a dichloroacetamide compound represented by the following formula (2):

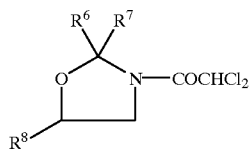

(2)

wherein $R^6$ and $R^7$ are independently hydrogen atom or an alkyl group having 1 to 3 carbon atoms; and $R^8$ is a heteroaryl group having 3 to 8 ring member carbon atoms and 1 to 2 hetero atoms selected from the group consisting of oxygen atom, sulfur atom and nitrogen atom, an alkyl group having 1 to 3 carbon atoms or hydrogen atom, and the heteroaryl group may be substituted by at least one substituent selected from the group consisting of an alkyl group having 1 to 3 carbon atoms, a halogen atom, an alkoxyl group having 1 to 3 carbon atoms, an alkylthio group having 1 to 3 carbon atoms, cyano group, nitro group and amino group, or a compound represented by the following formula (3):

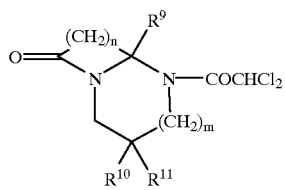

(3)

wherein $R^9$, $R^{10}$ and $R^{11}$ are independently a hydrogen atom or an alkyl group having 1 to 2 carbon atoms, n is 2 or 3, and m is 0 or 1, and an ethenylamide compound represented by the following formula (1) as a herbicidally effective component:

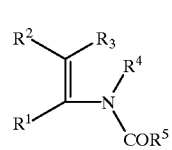

(1)

wherein $R^1$ is a heteroaryl group having 3 to 8 ring member carbon atoms and 1 to 2 hetero atoms selected from the group consisting of oxygen atom, sulfur atom and nitrogen atom, or aryl group having 6 to 14 carbon atoms, the heteroaryl group and the aryl group may be substituted by at least one substituent selected from the group consisting of an alkyl group having 1 to 3 carbon atoms, a halogen atom, an alkoxyl group having 1 to 3 carbon atoms, an alkylthio group having 1 to 3 carbon atoms, cyano group, nitro group and amino group; $R^2$ and $R^3$ are independently hydrogen atom or an alkyl group having 1 to 12 carbon atoms, or may be bonded together with the carbon atom, to which they are bonded, to form a ring having 5 to 6 ring member carbon atoms; $R^4$ is an alkyl group having 1 to 12 carbon atoms, an alkenyl group having 2 to 12 carbon atoms, an alkynyl group having 2 to 12 carbon atoms, an aryl group having 6 to 14 carbon atoms, a heteroaryl group having 3 to 8 carbon atoms, a cycloalkyl group having 3 to 6 carbon atoms, a cycloalkenyl group having 4 to 6 carbon atoms or a heterocycloalkyl group having 4 to 5 carbon atoms, all of these groups may be substituted by at least one substituent selected from the group consisting of an alkyl group having 1 to 3 carbon atoms, a halogen atom, an alkoxyl group having 1 to 3 carbon atoms, an alkylthio group having 1 to 3 carbon atoms, cyano group, nitro group and amino group, provided that when $R^4$ is an alkyl group having 1 to 12 carbon atoms or an alkenyl group having 2 to 12 carbon atoms, the substituent cannot be an alkyl group having 1 to 3 carbon atoms; and $R^5$ is a heteroaryl group having 3 to 8 ring member carbon atoms and 1 to 2 hetero atoms selected from the group consisting of oxygen atom, sulfur atom and nitrogen atom, an aryl group having 6 to 14 carbon atoms or an alkyl group having 1 to 12 carbon atoms, all of these groups may be substituted by at least one substituent selected from the group consisting of an alkyl group having 1 to 3 carbon atoms, a halogen atom, an alkoxyl group having 1 to 3 carbon atoms, an alkylthio group having 1 to 3 carbon atoms, cyano group, nitro group and amino group, provided that when $R^5$ is an alkyl group having 1 to 12 carbon atoms, the substituent cannot be an alkyl group having 1 to 3 carbon atoms.

5. A herbicidal composition comprising:

an ethenylamide compound represented by the following formula (1) as a herbicidally effective component:

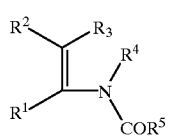
(1)

wherein $R^1$ is a heteroaryl group having 4 to 5 ring member carbon atoms and 1 hetero atom selected from the group consisting of oxygen atom, sulfur atom and nitrogen atom, or aryl group having 6 to 10 carbon atoms, the heteroaryl group and the aryl group may be substituted by at least one substituent selected from the group consisting of an alkyl group having 1 to 3 carbon atoms, a halogen atom, an alkoxyl group having 1 to 3 carbon atoms, an alkylthio group having 1 to 3 carbon atoms, cyano group and nitro group; $R^2$ and $R^3$ are independently hydrogen atom or an alkyl group having 1 to 3 carbon atoms, or may be bonded together with the carbon atom, to which they are bonded, to form a ring having 5 to 6 ring member carbon atoms; $R^4$ is an alkyl group having 1 to 5 carbon atoms, an aryl group having 6 to 10 carbon atoms, a heteroaryl group having 4 to 5 carbon atoms, all of these groups may be substituted by at least one substituent selected from the group consisting of an alkyl group having 1 to 3 carbon atoms, a halogen atom, an alkoxyl group having 1 to 3 carbon atoms, an alkylthio group having 1 to 3 carbon atoms, and $R^5$ is a heteroaryl group having 4 to 5 ring member carbon atoms and 1 hetero atom selected from the group consisting of oxygen atom, sulfur atom and nitrogen atom, an aryl group having 6 to 10 carbon atoms or an alkyl group having 1 to 3 carbon atoms, all of these groups may be substituted by at least one substituent selected from the group consisting of an alkyl group having 1 to 3 carbon atoms, a halogen atom, and an alkoxyl group having 1 to 3 carbon atoms; and a dichloroacetamide compound as a safener, wherein the dichloroacetamide compound is represented by the following formula (2)

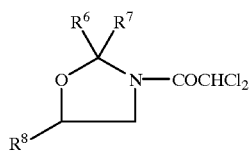
(2)

wherein $R^6$ and $R^7$ are independently hydrogen atom or an alkyl group having 1 to 3 carbon atoms; and $R^8$ is a heteroaryl group having 4 to 5 ring member carbon atoms and 1 hetero atom selected from the group consisting of oxygen atom, sulfur atom and nitrogen atom, an alkyl group having 1 to 3 carbon atoms or hydrogen atom, and the heteroaryl group may be substituted by at least one substituent selected from the group consisting of an alkyl group having 1 to 3 carbon atoms, or a compound represented by the following formula (3):

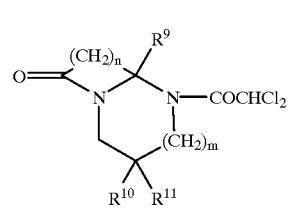
(3)

wherein $R^9$, $R^{10}$ and $R^{11}$ are independently a hydrogen atom or an alkyl group having 1 to 2 carbon atoms, n is 2 or 3, and m is 0 or 1.

6. The herbicidal composition of claim 5, wherein the dichloroacetamide compound is represented by the following formula (2):

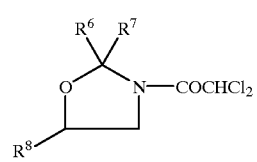
(2)

wherein $R^6$ and $R^7$ are independently hydrogen atom or an alkyl group having 1 to 3 carbon atoms; and $R^8$ is a heteroaryl group having 4 to 5 ring member carbon atoms and 1 hetero atom selected from the group consisting of oxygen atom, sulfur atom and nitrogen atom, an alkyl group having 1 to 3 carbon atoms or hydrogen atom, and the heteroaryl group may be substituted by at least one substituent selected from the group consisting of an alkyl group having 1 to 3 carbon atoms.

7. The herbicidal composition of claim 5, wherein the dichloroacetamide compound is represented by the following formula (3):

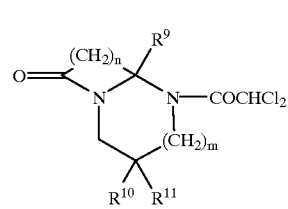
(3)

wherein $R^9$, $R^{10}$ and $R^{11}$ are independently a hydrogen atom or an alkyl group having 1 to 2 carbon atoms, n is 2 or 3, and m is 0 or 1.

* * * * *